(12) United States Patent
Kinsley et al.

(10) Patent No.: US 8,123,694 B2
(45) Date of Patent: Feb. 28, 2012

(54) ELECTRO PNEUMATIC INTERFACE FOR BLOOD PRESSURE SYSTEM

(75) Inventors: Matthew J. Kinsley, Liverpool, NY (US); John A. Lane, Weedsport, NY (US); Scott A. Martin, Warners, NY (US); Tyson B. Whitaker, Arden, NC (US); Thomas J. Grant, Skaneateles, NY (US); Joseph D. Buchanan, Waynesville, NC (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 887 days.

(21) Appl. No.: 12/175,657

(22) Filed: Jul. 18, 2008

(65) Prior Publication Data

US 2010/0016737 A1    Jan. 21, 2010

(51) Int. Cl.
*A61B 5/02* (2006.01)
(52) U.S. Cl. .................. 600/492; 600/485; 600/490
(58) Field of Classification Search .............. 600/481, 600/485, 490, 492; 285/921; 137/861; 200/61.86, 200/81 R; 439/190
See application file for complete search history.

(56) References Cited

U.S. PATENT DOCUMENTS

| 2,678,040 | A | | 5/1954 | Poole et al. | |
|---|---|---|---|---|---|
| 2,714,379 | A | | 8/1955 | Raines | |
| 3,659,592 | A | | 5/1972 | Natkanski | |
| 4,248,241 | A | | 2/1981 | Tacchi | |
| 4,488,139 | A | * | 12/1984 | Snider, Jr. | 439/23 |
| 4,605,010 | A | * | 8/1986 | McEwen | 600/499 |
| 4,896,676 | A | | 1/1990 | Sasaki | |
| 5,220,925 | A | | 6/1993 | Hishida | |
| 5,692,512 | A | * | 12/1997 | Flachslaender | 600/490 |
| 6,152,880 | A | | 11/2000 | Okada | |
| 6,183,417 | B1 | * | 2/2001 | Geheb et al. | 600/301 |
| 6,251,080 | B1 | | 6/2001 | Henkin et al. | |
| 6,344,025 | B1 | | 2/2002 | Inagaki et al. | |
| 6,450,966 | B1 | | 9/2002 | Hanna | |
| 6,475,153 | B1 | | 11/2002 | Khair et al. | |
| 6,506,162 | B1 | | 1/2003 | Tseng | |
| 2002/0147404 | A1 | | 10/2002 | Hiroyuki et al. | |
| 2007/0093718 | A1 | * | 4/2007 | Lane et al. | 600/494 |
| 2008/0114221 | A1 | * | 5/2008 | Tso | 600/301 |
| 2008/0243010 | A1 | * | 10/2008 | Kulik | 600/499 |
| 2009/0118628 | A1 | * | 5/2009 | Zhou et al. | 600/499 |
| 2009/0318818 | A1 | * | 12/2009 | Whitaker et al. | 600/495 |
| 2011/0046494 | A1 | * | 2/2011 | Balji et al. | 600/499 |

OTHER PUBLICATIONS

International Search Report for PCT/US2009/050621, mailed Mar. 11, 2010 (10 pages).

* cited by examiner

*Primary Examiner* — Patricia Mallari
*Assistant Examiner* — Meredith Weare
(74) *Attorney, Agent, or Firm* — Sonny Z. Zhan (57) ABSTRACT

A blood pressure system that includes a compact monitor housing that contains a pneumatic circuit and an electrical circuit and a processor for inflating and deflating a cuff to provide blood pressure related data. A split connector allows the housing to interface both pneumatically and electronically with one or more independent cuffs and/or with one or more host stations. Each host station contains a dependent cuff and further electrical components to expand and enhance the systems output of related blood pressure data that is generated by either the independent or dependent cuffs.

12 Claims, 6 Drawing Sheets

ELECTRO PNEUMATIC INTERFACE FOR BLOOD PRESSURE SYSTEM

FIELD OF THE INVENTION

This invention relates to a blood pressure system having a compact hand-held blood pressure reading unit that can be both electrically and pneumatically connected to one or more independent blood pressure cuffs or alternatively to one or more host stations, each of which contains a dependent blood pressure cuff.

BACKGROUND OF THE INVENTION

Most non-invasive blood pressure units generally include a blood pressure cuff that can be wrapped around a patient's limb over an artery. Blood pressure readings are typically obtained by initially inflating the cuff to a pressure that is high enough to constrict the flow of blood through the artery and the pressure in the cuff is then reduced under controlled conditions. Because the patient's heart is pumping blood through the constrained artery, the cuff pressure which is typically measured by a pressure sensor will include pressure changes produced by the blood flow which are superimposed upon the changing cuff pressure as the cuff is being deflated so that both a patient's systolic and diastolic blood pressure can be determined.

Systolic pressure is the maximum arterial pressure that is produced during contraction of the left ventricle of the heart. Diastolic pressure is the minimum arterial pressure that occurs during relaxation and dilation of the heart ventricles during which time the ventricles are filling with blood. Using the well known oscillometric method, the blood pressure cuff is initially inflated to a pressure that is greater than the highest expected systolic reading. The cuff is then deflated to a pressure that is less than the expected diastolic pressure. Above the systolic pressure, the pressure sensor readings reflect only the cuff pressure. When the cuff pressure falls to the systolic blood pressure level, the pressure signals indicate the presence of oscillations which are now superimposed upon the falling cuff pressure. When the cuff pressure falls below the diastolic pressure, the oscillations are no longer present on the cuff pressure signals. These two events can thus be recorded and further processed to provide valuable information concerning the condition of a patient's heart and his or her general health.

In many health care facilities, such as a doctor office, a single non-invasive blood pressure cuff may sometimes be used on a large number of patients during the day before the cuff is sanitized. Accordingly, cross contamination between ill patients can occur. In many other health care facilities, particularly where many of the patient's are confined to bed, the blood pressure units are mounted upon mobile carriages that can be transported between patient locations. Typically the various system components that are mounted upon the carriage are interconnected by lengthy electrical wires and pneumatic tubes. These connections invariably become entangled and pose a hazard to both health care workers and patients alike.

SUMMARY OF THE INVENTION

It is a primary object of the present invention to provide a blood pressure system that includes a compact hand-held blood pressure reader or monitor that can be interchangeably used with either a plurality of independent blood pressure cuffs or one or more host stations each of which contains dependent blood pressure cuffs to provide blood pressure readings and related data.

A further object of the present invention is to provide a small hand-held blood pressure reader that can communicate with one or more independent blood pressure cuffs or one or more host stations each of which contains a dependent cuff through a tubeless pneumatic connection and/or a wireless electrical connections.

A still further object of the present invention is to reduce the danger of cross contamination in non-invasive blood pressure systems.

Yet another object of the present invention is to reduce the size, weight and mobility of non-invasive blood pressure devices.

These and other objects of the present invention are attained by a blood pressure system having a compact handheld device that contains both electric and pneumatic circuitry that can be connected directly to one or more independent blood pressure cuffs or alternatively to one or more host stations, each of which contains a dedicated blood pressure cuff, to inflate and deflate the cuff to provide a patient's blood pressure data which can be visually displayed and/or stored in the unit.

BRIEF DESCRIPTION OF THE DRAWING

For a better understanding of these and other objects of the present invention reference will be made to the following detailed description of the of the invention which is to be read in association with the accompanying drawings, wherein.

DESCRIPTION OF THE INVENTION

Figure 8:
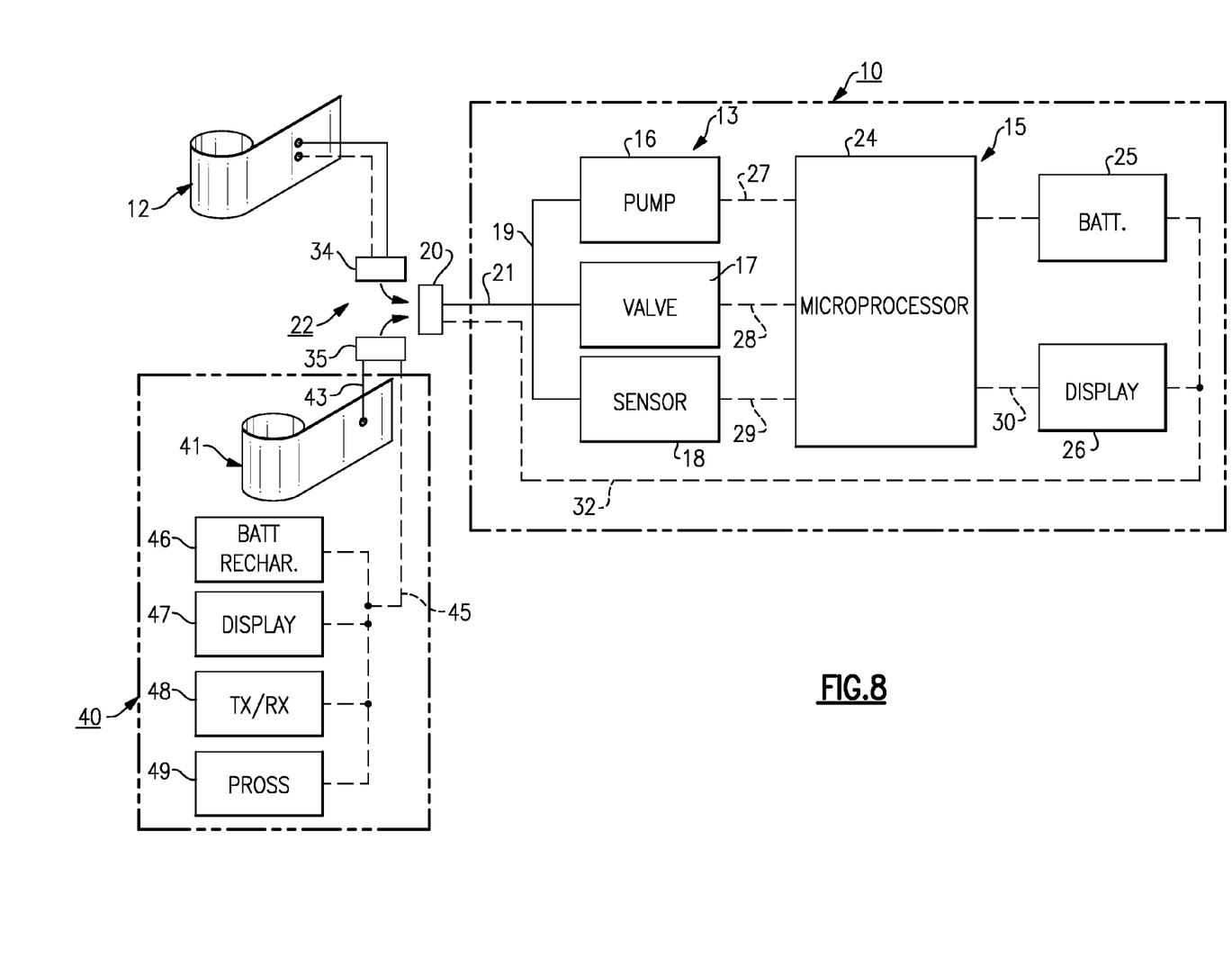
FIG. 8 is a block diagram showing the interrelationship of the component parts of the present blood pressure system.

Turning initially to FIG. 8, there is illustrated a block diagram that shows the component parts of a non-invasive blood pressure system that embodies the present invention. The system includes a compact housing generally referenced by 10 that contains a pneumatic circuit 13 and an electrical circuit 15. As will be explained in greater detail below, the two circuits 13, 15 are arranged to co-act under preprogrammed conditions to inflate and deflate a blood pressure cuff 12 to determine a patient's systolic and diastolic blood pressure readings. The pneumatic circuit 13 and the electrical circuit 15 are independently connected to a first receptor 20 of a two part interface connector 22. The term "receptor" as herein used refers to any type of connector that can be mated or closed with a similar type of connector so that one or more circuits in one component can communicate with one or more compatible circuits in another component. The first receptor 20 is arranged to mate or close with either one of two second receptors 34 or 35. One or more independent inflatable cuffs, such as cuff 12, may be equipped with a second receptor 34 that is mounted in the apron of each blood pressure cuff. Receptor 20 is arranged to mate with the second receptor 34 to minimally establish a hoseless connection between the cuff bladder and the pneumatic circuit 13 in the housing 10. Preferably, the two receptors 20 and 34, when closed, will also establish a wireless connection between the electrical circuit 15 and at least one electrical component mounted in the cuff 12.

Similarly, first receptor 20 can alternately close with a second receptor 35 that is mounted in one or more host stations 40, each of which contains a dependent blood pressure cuff 41. Here again, when the two receptors 20 and 35 are closed, a hoseless connection is made between the pneumatic circuit 13 in housing 10 and a pneumatic flow line 43 within the host station that services the dependent cuff 41. A wireless connection is also made at closure between the electric circuit 15 and a series of electrical components that are located with the host station 40 that serve to enhance and extend the operability of the system.

With further reference to FIG. 8, the pneumatic circuit 13 that is contained within the compact housing includes a pump 16 for inflating a cuff and a control valve 17 for deflating the cuff along with a pressure sensor 18 for sensing the cuff pressure. The three noted pneumatic components are all connected to a common flow line 19 which, in turn, is attached to line 21 leading to first receptor 20 of the two part connector interface 22. The electrical circuit 15 includes a microprocessor 24 that contains a memory, a rechargeable battery 25 and a display screen 26. The microprocessor 24 is coupled to each of the pneumatic components 16, 17, 18 via lines 27-29 and acts as a programmable controller in the system to regulate the pump and valve as well as initial processing of the output of the pressure sensor 18. The processed pressure related data is delivered via line 30 to the visual display 26 mounted within the housing 10 where it is visually presented to the system user. The battery 25 is arranged to deliver power to each of electrical components located in the housing 10. These electrical components are connected to the first receptor 20 via a common electric harness 32.

The first receptor 20 can also be releasably coupled to the second receptor 35 that is mounted upon one or more host stations 40 which normally are located at a fixed location within a medical facility. The first receptor 20 has both a pneumatic connection and an electrical connection which are arranged to couple with the pneumatic and electrical circuits in the monitor housing. Each host station 40 contains its own inflatable cuff 41 that is coupled to the pneumatic side of the second receptor 35 by pneumatic line 43. Each host station 40 may also include a number of electrical components that are coupled to the electrical side of the second receptor 35 by an electrical harness that is identified as 45. The electrical components housed in each host station 40 may vary from station to station but typically will include a battery charging unit 46, an enlarged display panel 47 and a communication system 48 that might be hard wired within a medical facility or communicate wirelessly with one or more other remote facilities. Each host station 40 may also include an additional computer 49 that is capable of downloading the initially processed data and other related data from the monitor housing and further processing the data. The host station computer 49 can also be used for keeping the records of a large number of patients within a given facility and providing other patient related data.

It is envisioned that the present blood pressure system may be used in a medical facility wherein each patient is issued his or her own blood pressure cuff having a receptor 34 that mates with receptor 20 of the monitor housing 10. Periodically, the data stored in the monitor can be downloaded into a host station computer or sent to a remote location for further processing. Alternatively, the system may be utilized in a smaller facility, such as a doctor's office with the host station being situated in the doctor's examination room. In this type of arrangement, the blood pressure of patients waiting in the reception area can be loaded into the monitor housing 10 and the data then transferred to the host station unit thus saving a considerable amount of time during an average day.

Figure 1:
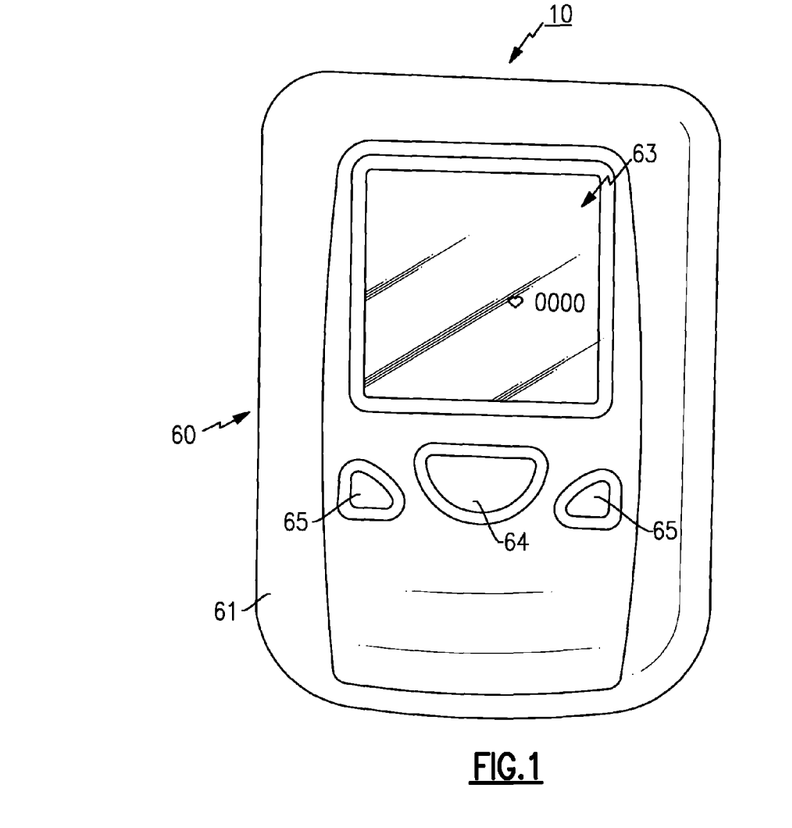
FIG. 1 is a front view of a hand-held blood pressure housing unit that contains a pneumatic circuit and an electric circuit that coact to automatically take blood pressure readings when the unit is coupled to a non-invasive blood pressure cuff or a host station that contains a dedicated blood pressure cuff.
Figure 2:
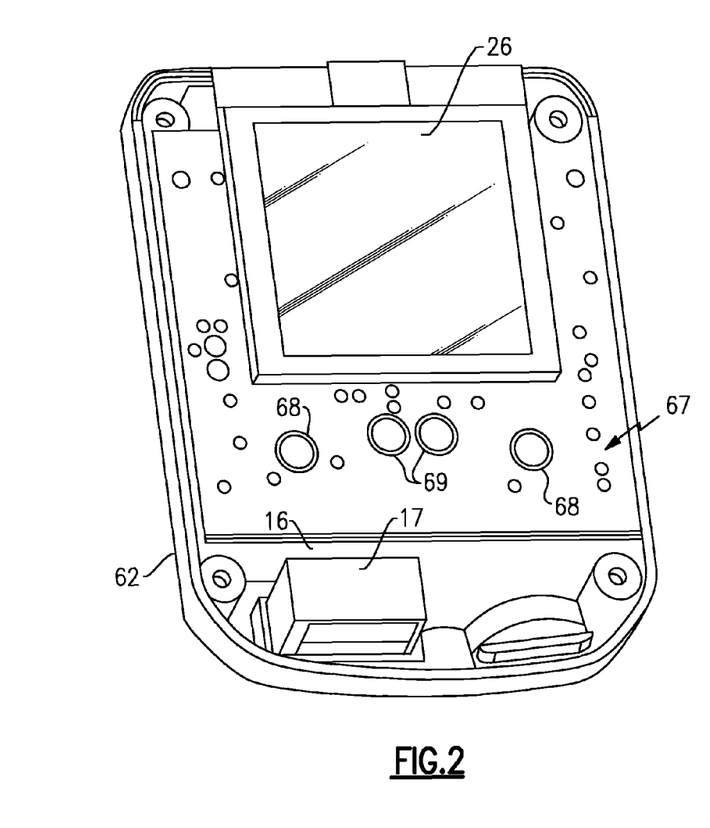
FIG. 2 is a front view similar to that illustrated in FIG. 1 with the housing cover being removed.
Figure 3:
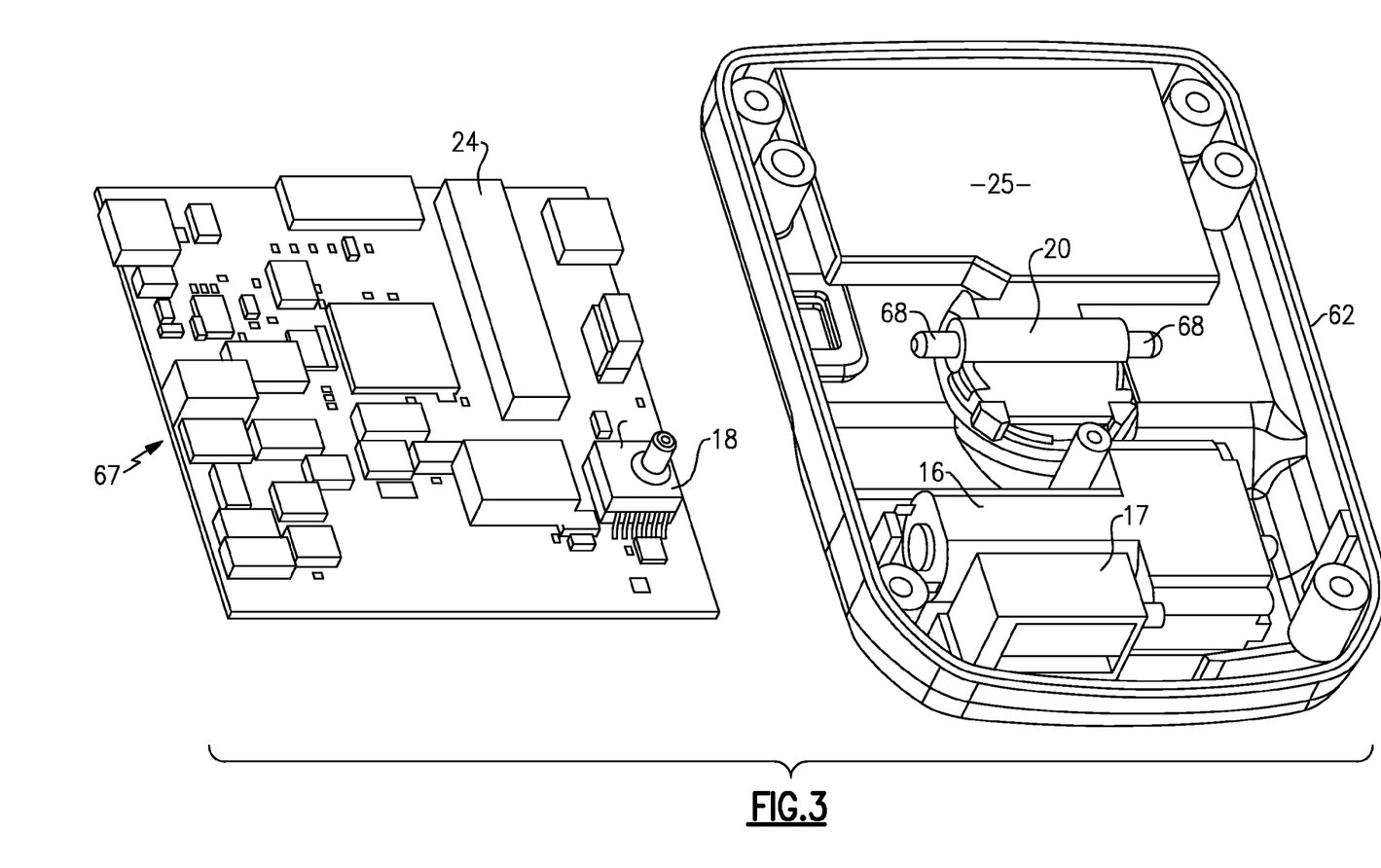
FIG. 3 is a further front view of the unit shown in FIG. 2 with its printed circuit board removed to more clearly show certain components that are contained within the unit housing.

Turning now to FIGS. 1-3, the blood pressure monitor housing 60 is shown in further detail. The housing as illustrated in FIG. 1 is a compact unit being approximately 4.0" in height, 2½" in width and about ⅞" in depth so that it can be easily supported upon a cuff when the receptor 20 of the connector unit is snap-fitted into the receptor 34, FIG. 8, mounted upon a blood pressure cuff. The housing 60 includes a removable face plate or cover 61 that is connected to a bottom section or bay 62 by means of screws or the like. The face plate 61 further contains a window 63 through which a read out screen 26 located in the bay can be viewed. A series of user accessible buttons 64 and 65 are mounted in the face plate 61 immediately below the window 63. The buttons 64, 65 provide for user interaction with the microprocessor 24 and other components that are stored in the bay. Such interaction may include but are not limited to the initiation of a blood pressure reading cycle, calling for a readout of some previously stored data or the like, or setting into the microprocessor patient related data, as well as times and dates relating to specific pressure readings.

FIG. 2 illustrates the housing with the cover 61 removed so that some of the stored components can be seen. A video screen 26 is mounted on the backside of a printed circuit board 67 so that the data presented upon the screen can be easily read through the face plate window 26. A series of function switches 68 and 69 are also mounted on the circuit board 67 in a location so that they can be activated by the activator buttons 64 and 65. A portion of the system pump 16 can be seen beneath the circuit board 67 with the system discharge valve 17 being positioned immediately beneath the pump.

FIG. 3 illustrates the open bay of the housing with the circuit board 67 removed and turned over on the left hand side of the bay. A rechargeable battery 25 is mounted upon the floor of the bay and, as pointed out above, is connected to both the pneumatic and electrical circuits by a suitable wiring harness 32, FIG. 8, and conductive traces printed upon the circuit board (not shown). The pump 16 can be more plainly seen in this view. The microprocessor 24 is mounted on the backside of the circuit board 67 along with a pressure sensor 18. It should be understood that the pump, valve and pressure sensor are connected by tubing which has been removed the view for the sake of clarity. The back side of the receptor 20 of the integrated connector unit is shown centrally located on the floor of the bay and includes a pair of tubular connectors 68-68, which couple the receptor to the pneumatic circuit components that are stored in the bay.

Figure 4:
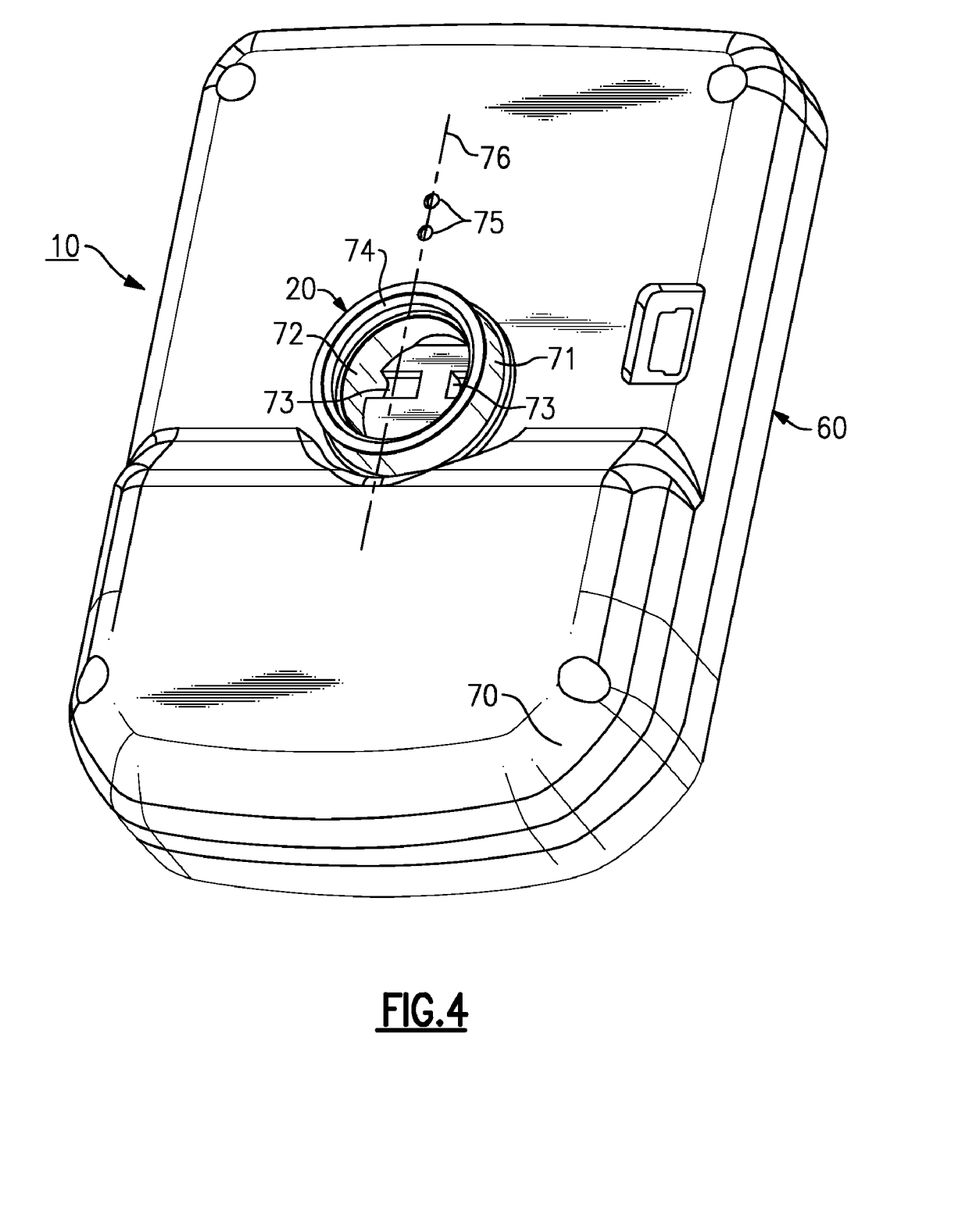
FIG. 4 is a perspective view illustrating the back of said housing, which contains an integrated electric/pneumatic interface that permits the housing to be interchangeably connected to either one or more inflatable blood pressure cuffs or one or more host stations each of which contains a dedicated cuff.

FIG. 4 illustrates the back panel 70 of the blood pressure monitor housing and in particular the face of the receptor 20 of the integrated connector unit 22. This section includes a cylindrical hub 71 having a circular port 72 that is in fluid flow communication with the previously noted tubular connectors 68-68, FIG. 3, via openings 73-73. The inner surface of the hub port contains a circular groove 74 formed therein, the purpose of which will be explained in further detail below. Also located on the back panel of the bay are two electrical conductor pads 75-75. The pads 75-75 are spaced apart along a common centerline 76 that passes through the center of the hub. The pads pass 75-75 into the bay of the housing and are electrically coupled to the harness 32 that services the electrical and pneumatic circuits of the monitor housing.

Figure 5:
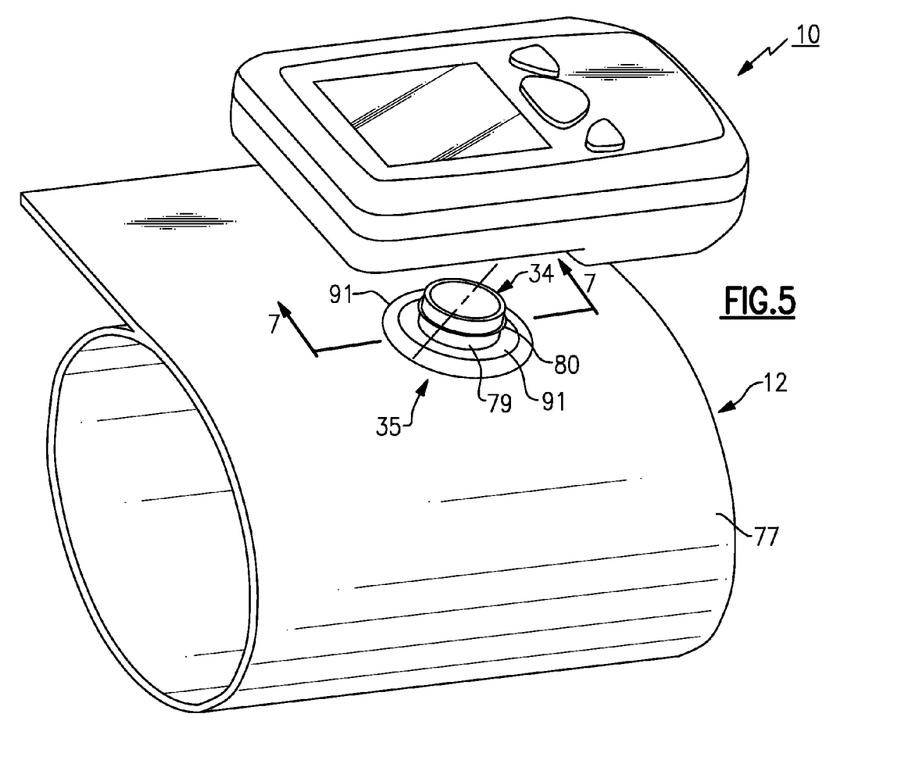
FIG. 5 is a perspective view showing the unit housing being positioned adjacent to an inflatable blood pressure cuff prior to coupling the housing to the cuff.

FIG. 5 illustrates the blood pressure monitor 10 positioned over the sleeve 77 of cuff 12 with the housing receptor 20 aligned with the cuff receptor 34 of the integrated connector unit 22. The receptor 34 includes a cylindrical tube 79 made of hard rubber or a similar type of material having a given amount of resiliency. The outer diameter of the tube 79 is slightly greater than that of the circular port in the receptor 20 so that the tube can be press fitted into the port 72 to establish a leak-tight running fit between the two coupled members. A circular bead 80 extends around the outer surface of the tube which seats within the groove 74 (FIG. 4) formed in the hub of the receptor 20 to insure proper closure of the receptor. When the connector unit is closed, the monitor housing can be rotated about the tube without breaking the leak tight joint between the two receptor members thus, allowing the monitor to be moved into an infinite number of positions and enhancing the users ability to accurately read the data present upon the read out screen 68, FIG. 2.

Figure 7:
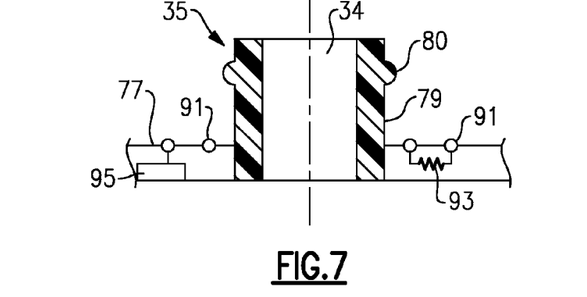
FIG. 7 is an enlarged sectioned view of the interface taken through line 7-7 of FIG. 5.

Turning now to FIG. 7 which is a section taken through the apron of a cuff 12, there is shown a pair of circular conductors 91-91 that surround the tube 79 and are spaced with regard to the tube so that the pad 75 will close against the conductor when the receptor 20 is closed against the receptor 34. This, in turn, places the cuff 12 in electrical communications with the electric circuit contained in the monitor housing which includes the microprocessor. A resistor 93 may be mounted in the apron of the cuff which is connected over the circular conductors 91-91 to provide a signal to the microprocessor which identifies the cuff size by the size of the resistor. In addition, an electronically readable microchip 95 can be also mounted inside the apron of the cuff 12, FIG. 5, which contains a cuff identification number or any other suitable cuff identifying information that can be read by the microprocessor. The identification information allows the cuff 12 to be associated with a patient to which it is issued helping to bring together patient related data with the related blood pressure data.

Figure 6:
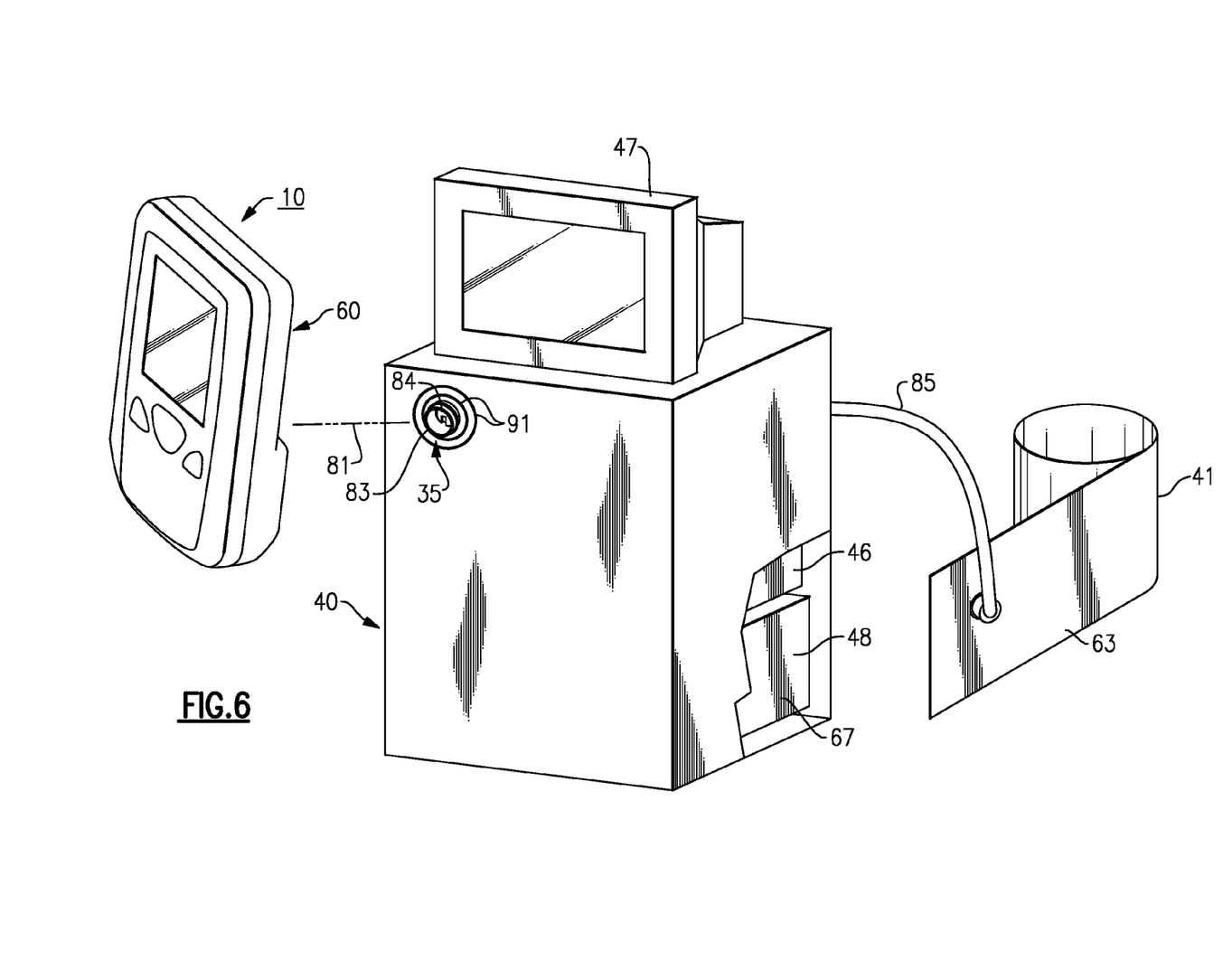
FIG. 6 is a perspective view showing the unit housing position adjacent to a host station prior to the housing being coupled to the host station.

FIG. 6 illustrates the monitor housing 60 positioned with regard to a host station 40 so that the receptor 20 is aligned with the host station receptor 35 along a common center line 81 whereby the receptors can be co-joined snap fitted together. Here again, the receptor 35 contains a cylindrical hard rubber tube 83 having a circular bead 84 surrounding the tube as explained above. The receptor 35 thus can be fitted into the port 72 of the housing receptor 20 to establish a leak-tight joint between the mated receptors. As in the preceding, the monitor housing can be rotated about the tube without breaking the leak tight joint. The host station 40 contains its own dedicated cuff 41 that is connected to the receptor 35 by a flexible lumen 85. The station 40, as noted above, contains an expanded viewing screen 47 and a series of electronic components for expanding the functionality of the system. The viewing screen 47 and electronic components are connected internally to a pair of circular electrically spaced apart contacts 91-91 that surround the tube of receptor 35 and share the common centerline. The circular contacts 91-91 are set at a radius from the center of the tube 83 as are the two contacts 75-75 (FIG. 4) on the receptor 34 connector. Accordingly, once an electrical connection is established between the monitor and the host station, the electrical connection will remain unbroken as the monitor housing is rotated about the axis of the tube 83.

While the invention has been described with reference to preferred embodiments, it will be understood by those skilled in the art that various changes may be made and equivalents may be substituted for elements thereof to adapt to particular situations without departing from the scope of the invention. Therefore, it is intended that the invention not be limited to the particular embodiments disclosed as the best mode contemplated for carrying out this invention, but that the invention will include all embodiments falling within the scope and spirit of the appended claims.

The invention claimed is:

1. A blood pressure system comprising:
   a compact housing that contains a pneumatic circuit that includes a pump for inflating a blood pressure cuff, a valve for deflating said cuff, a pressure sensor for providing cuff pressure data and an electrical circuit having a control means for programming said pneumatic circuit and for processing cuff pressure data;
   said housing further including a display means for visually presenting said processed data; and
   a split connector comprising:
      a female member mounted upon said housing, and
      a male member mounted upon one or more independent blood pressure cuffs or alternatively one or more host stations, wherein each host station contains a dedicated blood pressure cuff,
   wherein said female member is adapted to releasably close with said male member to establish a hoseless connection between said pneumatic circuit and said one or more independent cuffs and said one or more host stations and a wireless electrical connection between said electrical circuit and said one or more host stations,
   wherein said split connector also establishes a wireless electrical connection between said electrical circuit and said one or more independent cuffs when said split connector is closed,
   wherein said hoseless pneumatic connection provides a leak-tight joint between said female member and said male member when said members are brought together at closure,
   wherein said wireless electrical connection includes one or more first electrical contacts mounted adjacent to one of said female member and said male member that ride in sliding contact with one or more second electrical contacts encircling the other of said female member and male member when the two receptors are brought together at closure and when said housing is rotated about an axis of said split connector.

2. The blood pressure system of claim 1, wherein said housing further contains a rechargeable battery for providing power to electrical components contained in said housing.

3. The blood pressure system of claim 2, wherein said host station further includes means for recharging said rechargeable battery when said split connector is closed.

4. The blood pressure system of claim 3, wherein said host station contains additional processing means for further storing and processing blood pressure related data from said microprocessor when said split connector is closed.

5. The blood pressure system of claim 4, wherein said host station further includes an enlarged display for visually presenting blood pressure related data.

6. The blood pressure system of claim 5, wherein said host station further includes a bi-directional communication unit for exchanging blood pressure related data with at least one other station.

7. The blood pressure system of claim 1, wherein said control means is a microprocessor that contains storage means for storing blood pressure related data.

8. The blood pressure system of claim 1, wherein said one or more independent cuffs each contain a detecting means for providing an electrical signal to said control means which identifies the size of each cuff.

9. The blood pressure system of claim 8, wherein said detecting means is a resistor that is mounted in each cuff.

10. The blood pressure system of claim 1, wherein said one or more independent cuffs each contain an electronically readable chip that contains information for identifying said cuff.

11. The blood pressure system of claim 1, wherein said male member includes a cylindrical body and said female member includes a circular port for slidably receiving said male member therein.

12. The blood pressure system of claim 11, wherein said cylindrical body further includes a circular bead that encircles said body and said circular port includes a circular groove therein into which said bead is snap fitted when said male member and said female member are brought together at closure so that said housing can rotate about said axis of said split connector without breaking said leak-tight joint.

* * * * *